United States Patent [19]

White et al.

[11] Patent Number: 5,567,855

[45] Date of Patent: Oct. 22, 1996

[54] METHODS FOR STEREOSPECIFIC SYNTHESIS OF POLYENE ALDEHYDES

[75] Inventors: Steven K. White; Chan K. Hwang; David T. Winn, all of San Diego, Calif.

[73] Assignee: Ligand Pharmaceuticals Incorporated, San Diego, Calif.

[21] Appl. No.: 230,939

[22] Filed: Apr. 21, 1994

Related U.S. Application Data

[63] Continuation-in-part of Ser. No. 52,040, Apr. 21, 1996, abandoned.

[51] Int. Cl.⁶ .................................................. C07C 45/47
[52] U.S. Cl. .................................... 568/449; 568/483
[58] Field of Search .............................. 568/447, 483

[56] References Cited

U.S. PATENT DOCUMENTS

| | | | |
|---|---|---|---|
| 3,006,939 | 10/1961 | Pommer et al. | 260/413 |
| 4,523,042 | 6/1985 | Loev et al. | 554/221 |
| 5,094,783 | 3/1992 | Muccio et al. | 568/827 |
| 5,250,710 | 10/1993 | Chabardes et al. | 568/447 |

FOREIGN PATENT DOCUMENTS

| | | |
|---|---|---|
| 1050763 | 2/1959 | Germany . |
| 1068710 | 11/1959 | Germany . |
| 1068719 | 11/1959 | Germany . |
| 1174769 | 7/1964 | Germany . |

OTHER PUBLICATIONS

Aurell, M. J. et al., *Tetrahedron Letters*, vol. 31, No. 40, pp. 5791–57 94 (1990).

Bhattacherjee et al., *Ann. N.Y. Acad. Sci.*, 534:307 (1984).

Cainelli, G. et al., *J. C. S. Perkin I*, 1597–99 (1979).

Dugger, R. W., et al. *J. Org. Chem.*, 45:1181–85 (1980).

Gedye, R. N. et al., *Can J. Chem.*, vol. 53, No. 13, pp. 1943–48 19 (1975).

Heyman, R. A. et al., *Cell*, 68:397–406 (Jan. 24,1992).

Igbal, M. et al., *J. of Labelled Cds. & Radiopharmaceuticals*, vol. XXII, No. 8, pp. 807–817 (1985).

Kryshtal, G. V. et al., *Izvestiya Akademii Nauk SSSR, Serya Khimicheskaya*, No. 6, pp. 1414–1417 (Jun. 1990).

Kryshtal, G. V. et al., *Izvestiya Akademii Nauk SSSR, Seriya Ihimicheskaya*, No. 6, pp. 1417–1421 (Jun. 1990).

Kryshtal, G. V. et al., *Izvestiya Akademii Nauk SSSR, Seriya Khimicheskaya*, No. 11, pp. 2544–24 50 (Nov. 1990).

Matsui, M. et al., *J. Vitaminol*, 4:178–89 (1958).

Mayer, H. et al., *Experientia*, 34:1105–19 (1978).

Pattenden, G. et al., *J. Chem. Soc. (C)*, pp. 1984–1997 (1968).

Robeson, C. D. et al., *J. Am. Chem. Soc.*, 77:4111–19 (Aug. 5, 1955).

*Primary Examiner*—Gary Geist
*Assistant Examiner*—Deborah D. Carr
*Attorney, Agent, or Firm*—Lyon & Lyon

[57] ABSTRACT

Methods for stereospecific synthesis of 9-cis olefins and retinoids. In one particular aspect, a cis olefin is generated via a lactol ring opening with complete retention of double bond configuration.

4 Claims, No Drawings

METHODS FOR STEREOSPECIFIC SYNTHESIS OF POLYENE ALDEHYDES

RELATED APPLICATION

This application is a continuation-in-part of the application Ser. No. 08/052,040 filed on Apr. 21, 1993, now abandoned, whose entire disclosure is incorporated herein by reference.

FIELD OF THE INVENTION

The present invention relates to the stereospecific synthesis of polyene compounds, such as eicosanoids and retinoids. In one particular aspect, a cis olefin is generated via a lactol ring opening with complete retention of double bond configuration.

BACKGROUND OF THE INVENTION

In many examples of natural products, an extended conjugated olefinic chain is present and important for biological effects. Many of the compounds within the arachidonic acid cascade (eicosanoids) are important modulators of inflammation. For example, leukotriene B4 has been detected in fluid from involved tissue in rheumatoid arthritis, gout, psoriasis and ulcerative colitis. (Bhattacherjee et al., *Ann. N.Y. Acad. Sci.*, 524:307 (1984)). The absolute stereochemistry of the olefinic series is often an important feature of these compounds.

The retinoid members of the steroid/thyroid superfamily of receptors are responsive to compounds referred to as retinoids, which include retinoic acid, retinol (vitamin A), and a series of natural and synthetic derivatives which have been found to exert profound effects on development and differentiation in a wide variety of systems. Novel members of the steroid/thyroid superfamily of receptors have been identified which are not responsive to retinoic acid, called retinoid X receptors. 9-cis-retinoic acid has been demonstrated to have affinity for retinoid X receptors (Heyman et al., *Cell*, 68:397 (1992)), and other retinoids having 9–10 cis olefin geometry have been found to selectively activate retinoid X receptors.

Therefore, it would be advantageous to selectively prepare retinoid and retinoid-like compounds with the 9–10 olefin bond in a cis-configuration, and to prepare other polyene compounds having the desired stereochemistry.

The literature has examples of the preparation of 9–10 cis olefin retinoids, but none of which are specific in their construction of the 9–10 olefin bond. (See Robeson et al., *J. Am. Chem. Soc.*, 77:4111 (1955); Matsui, et al., *J. Vitaminol.*, 4:178 (1958); Pat. No. DE 1068719 (1958); Aurell, et al., *Tetrahedron Lett.*, 31:5791 (1990). The stereoselective preparation of the 13–14 olefin bond has been reported. (Pattenden et al., *J. Chem. Soc.* (*C*), 1984 (1968); Mayer et al., *Experientia*, 34:1105 (1978). Other information helpful in the understanding and practice of the present invention can be found in: U.S. Pat. Nos. 3,006,939 (1961); DE 1050763 (1959); DE 1174769 (1964); DE 1068710 (1959).

The entire disclosures of the publications and references referred to above and hereafter in this specification are incorporated herein by reference.

DETAILED DESCRIPTION OF THE INVENTION

In accordance with the present invention, we have developed methods to prepare 9-cis retinoids and other polyene compounds with very high selectivity of all olefin bond-forming reactions. Specifically, we have developed methods to prepare a trans/cis diene acyclic carbon skeleton from a lactol ring (Scheme 1), which can be used in the synthesis of cis-olefin containing natural or modified natural products, and synthetically-manufacuted analogs of such compounds. In a further aspect of the invention, we selectively prepare a trans/trans diene acyclic carbon skeleton by a modified Wittig coupling reaction (Scheme 2), as shown below.

Scheme 1: Stereospecific Generatin of a E/Z Olefin Chain

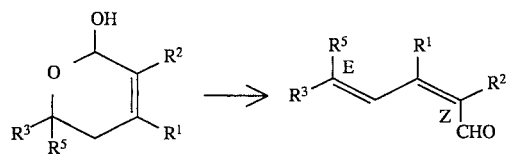

Scheme 2: Stereospecific Generatin of a E/E Olefin Chain

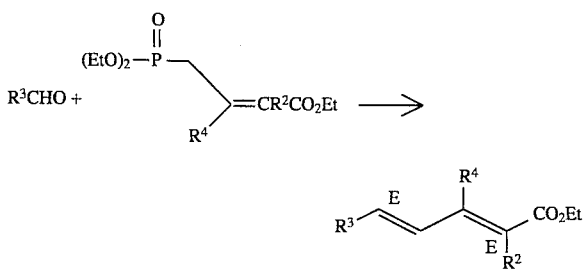

In the above process sequence, $R^1$ represents a lower or branched alkyl having 1–12 carbons, or phenyl, and can be methyl only if $R^2$ is hydrogen or a lower alkyl having 1–8 carbons;

$R^2$ represents hydrogen, a lower alkyl having 1–8 carbons, or halogen, or $R^1$ and $R^2$ taken together form a phenyl, cyclohexyl, or cyclopentyl ring;

$R^3$ represents a lower alkyl having 1–8 carbons, polyene compounds of the formula $R^1$—CH=CH—C($R^1$)=CH— (E or Z orientation), cycloalkyl, or aryl;

$R^4$ represents hydrogen, a lower alkyl having 1–8 carbons, or a halogen; and $R^5$ represents hydrogen, a lower alkyl having 1–8 carbons, or halogen.

Together and in sequence, we have developed preferred methods to prepare 9-cis retinoids in five steps with very high selectivity of all olefin bond-forming reactions. This sequence of steps is generally shown below:

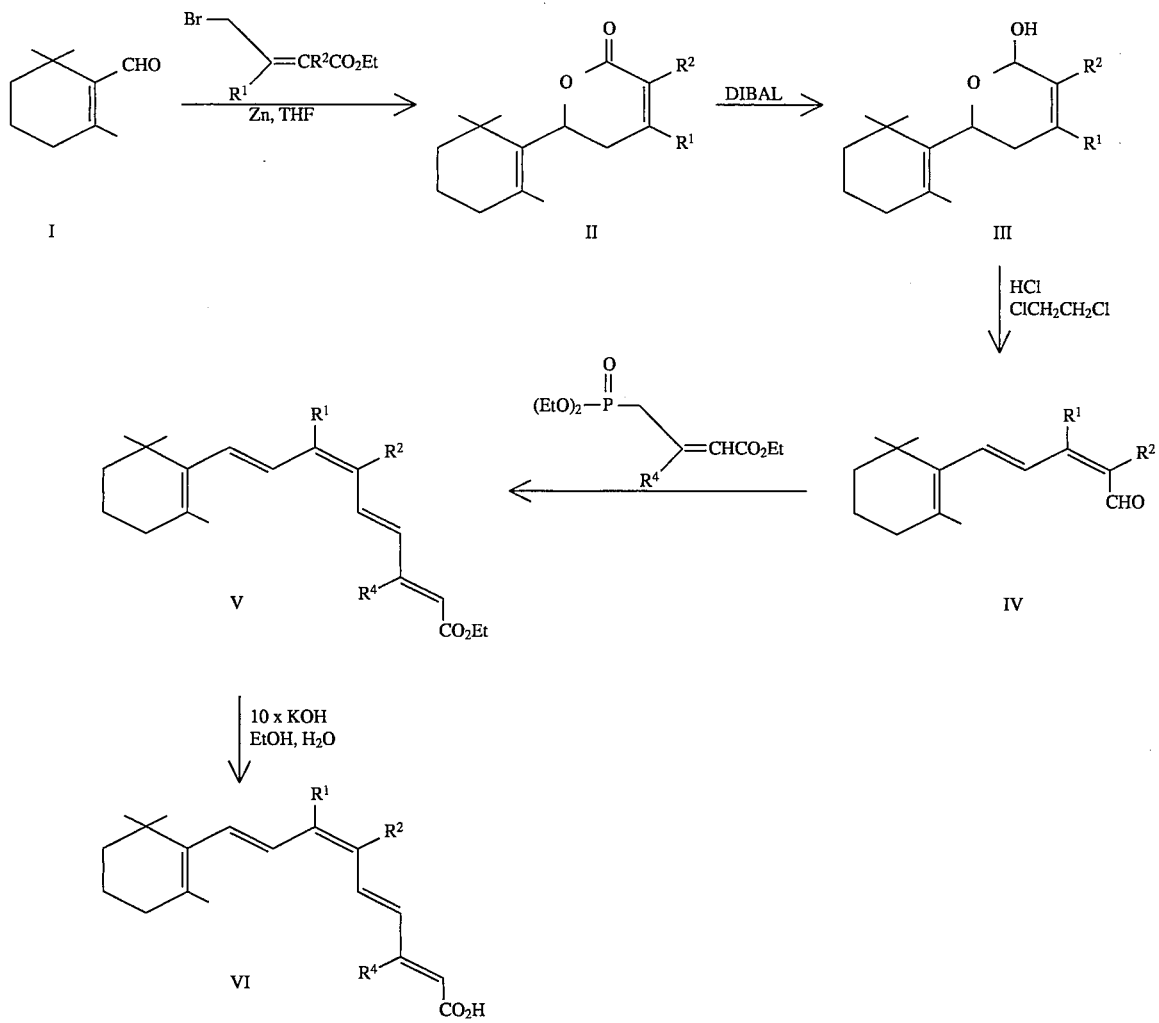

In the above process sequence, $R^1$ represents a lower or branched alkyl having 1–12 carbons, or phenyl, and can be methyl only if $R^2$ is hydrogen or a lower alkyl having 1–8 carbons;

$R^2$ represents hydrogen, a lower alkyl having 1–8 carbons, or halogen, or $R^1$ and $R^2$ taken together form a phenyl, cyclohexyl, or cyclopentyl ring or one of the following:

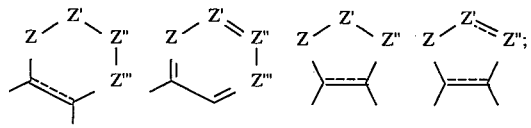

$R^3$ represents a lower alkyl having 1–8 carbons, polyene compounds of the formula $R^1$—CH=CH—C($R^1$)=CH— (E or Z orientation), cycloalkyl, or aryl;

$R^4$ represents hydrogen, a lower alkyl having 1–8 carbons, or a halogen;

Z, Z', Z", and Z'", each independently, represent C, S, O, N, or a pharmaceutically acceptable salt, but not O or S if attached by a double bond to another such Z or if attached to another such Z which is O or S, and not N if attached by a single bond to another such Z which is N; and the dashed lines in the structures depict optional double bonds.

Additional substitutions are also possible for the terminal COOH group of acid VI and can be readily made by those of skill in the art. For example, instead of COOH the terminal group may be tetrazole, $PO_3H$, $SO_3H$, CHO, $CH_2OH$, $CONH_2$, COSH, $COOR_9$, $COSR_9$, $CONHR_9$, or COOW where $R_9$ represents a lower alkyl having 1–4 carbons, phenyl, or q-hydroxyphenyl, q-bromophenyl, q-chlorophenyl, q-florophenyl, or q-idodophenyl, where q=2–4, and where W is a pharmaceutically acceptable salt.

As used in this disclosure, pharmaceutically acceptable salts include but are Not limited to: hydrochloric, hydrobromic, hydroiodic, hydrofluoriic, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those of skill in the art.

The preferred process sequence begins with the use of a commercially available aldehyde β-cyclocitral I and the well established Reformatsky reaction. (Dugger et al., *J. Org. Chem.*, 45:1181 (1980); Gedye et al., *Can. J. Chem.*, 53:1943 (1975); Cainelli et al., *J. C. S. Perkin I* 1597 (1979)). This step constructs the 9–10 olefin bond in the desired cis-orientation, as shown (II).

The second step consists of reduction of the lactone to a protected aldehyde (lactol) which is necessary for chain length extension. The reduction is achieved with 1 equivalent of diisobutylaluminum hydride and is sensitive toward work-up. We have found that the exclusion of water during the final purification of product greatly enhances the yield. Other reducing agents such as lithium aluminum hydride and sodium bis(2-methoxyethoxy) aluminum hydride can give the same product III but in diminished yield.

The third step of this sequence involves a unique and novel lactol ring opening under the presence of acid to afford the aldehyde IV. This step constitutes a major advantage over existing syntheses of the aldehyde IV previously reported in the literature. The ring opening is very sensitive to the pKa of the acid, the concentration of the acid, the concentration of the reactant in the solvents, and the temperature of the reaction. The reaction can be run in chlorinated solvents ($CHCL_3$, $CH_2CL_2$, $ClCH_2CH_2Cl$), apolar solvents (benzene, toluene), or coordinating solvents (diethylether, tetrahydrofuran). The choice of acids includes: para-toluene sulfonic acid, pyridinium hydrochloride, trichloro- or trifluoro-acetic acid, acetic acid, sulfuric acid, nitric acid, tartaric acid, oxalyic acid, and in particular hydrochloric acid. This third step can also be used to achieve the desired stereochemical orientation of olefin bonds for other polyene natural products, such as leukotriene $B_4$, dehydroneral, etc., and synthetic analogs. Illustrative examples of such compounds are shown below:

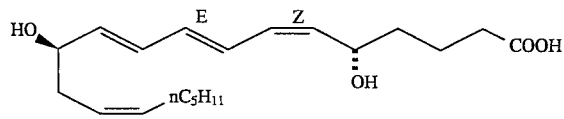

Leukotriene $B_4$

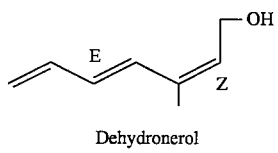

Dehydronerol

The fourth step of this sequence includes the selective formation of the C-11 and C-13 olefin bonds simultaneously. This reaction has been reported in the literature (Kryshtal et al., *Izvestiya Akad. Nauk USSR, Seriya Khim.*, 11:2544 (1990)), but never with better than 5:1 ratio of 13-trans to 13-cis olefin formation. We have found that using a lithium coupled base in tetrahydrofuran in the presence of a coordinating solvent, such as dimethyl piperidine urea, allows the formation of the 11,13-trans-olefin bonds in a greater than 15:1 ratio. Other solvents, including diethyl ether, 1,4-dioxane, t-butyl-methyl ether, dimethyl formamide, dimethyl sulfoxide, methanol, ethanol, benzene, toluene, dichloromethane, chloroform, pyridine, and acetonitrile are less effective for overall yield of the desired 11,13-ditrans olefin product. Other bases (e.g., sodium hydride, Sodium methoxide, sodium amide, potassium t-butoxide, potassium hydride, potassium di-isopropylamide, lithium diisopropylamide, lithium bis-trimethylsilylamide) are less effective than n-butyl lithium. The reaction can be completed at −78° C. or up to room temperature.

The hydrolysis of the ester V to the acid VI is a standard saponification reaction. We have found that the reaction proceeds better in ethanol than methanol due to the better solubility in the former solvent. One example of a VI compound is 9-cis-retinoic acid. 11-cis and 13-cis retinoids and other related compounds, as illustrated below, can also be prepared using this process scheme.

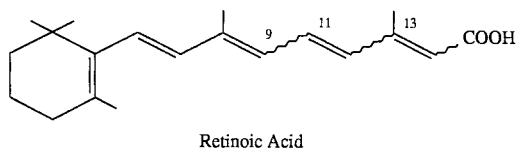

Retinoic Acid

The method of the current invention is shown by the following illustrative example.

EXAMPLE 5,6-Dihydro-4-methyl-6-(2,6,6-trimethyl-1-cyclohexen-1-yl)-2H-pyran-2-one (II, where $R^1$ is methyl and $R^2$ is hydrogen): In a 300 ml round-bottomed flask fitted with a reflux condenser, nitrogen inlet, and 125 ml addition funnel was added 8.34 grams of zinc dust and 15 ml of dry tetrahydrofuran. The β-cyclocitral (18.5 grams) and bromo-ester (25.2 grams) were added to the addition funnel with 50 ml of dry tetrahydrofuran. The reactants were added dropwise following an initial addition of 5 ml to initiate the reaction. The rate of addition was adjusted to maintain a gentle reflux, with ca. 45 min for complete addition. The reaction solution was then heated to reflux for 30 minutes. After cooling to room temperature, 50 ml of saturated ammonium chloride solution was added and the solution stirred for 30 min. The reaction solution was worked up with addition of another 100 ml of saturated ammonium chloride solution to a 500 ml separatory funnel and dimethyl ether extraction (3×75 ml). The combined organic layers were washed with brine and dried over $MgSO_4$. Concentration in vacuo produced 28.7 g (100%). The product was dissolved in 150 ml of hot hexane and allowed to recrystallize with cooling. The white solid was filtered and collected to yield 22.5 grams of II (78.4%). $^1$HNMR ($CDCl_3$, 400 MHz); d (ppm) 5.82 (s, 1H), 4.96 (dd, 13.4, 4.4 1H), 2.88 (dd, 13.4, 18.5, 1H), 2.16 (dd, 18.5, 3.4, 1H), 1.98 (s, 3H), 1.96 (m, 1H), 1.75 (s, 3H), 1.57–1.65 (m, 2H), 1.42–1.50 (m, 2H), 1.09 (s, 3H), 0.97 (s, 3H). IR (KBr, $cm^{-1}$): 2933, 1718, 1699, 1257.

5,6-Dihydro-4-methyl-6-(2,6,6-trimethyl-1-cyclohexen-1-yl)-2H-pyran-2-ol (III, where $R^1$ is methyl and $R^2$ is hydrogen): To 1.2 L of tetrahydrofuran (THF) was added the lactone (165 g). The resulting solution was cooled in a −78° C. bath and with constant stirring was aided DIBAL (920 ml, 1.0M in CH2C12) dropwise, never allowing the solution to warm above −40° C. (2 h addition time). After 15 minutes the reaction was complete, as evidenced by tlc ($Et_2O$/Hexane; 40:60). To the cooled solution was added 500 ml of 10% $H_2O$/THF as a quenching solution. The solution was removed from the bath and allowed to warm to room temperature, while monitoring the rate of warming. After reaching ca. 10°–15° C. there was noticed a significant exotherm with the precipitation of salts. This exotherm was retarded by use of the cooling bath again. At this point, 100 g of $Na_2SO_4$ was added and the resulting suspension was stirred for 0.5 hours. The solution was filtered through a bed of Celite, the bed washed with THF (2×500 mL) and the solution concentrated to yield an oil with solid ppt. The oil was slurred up in hexane (500 ml) and cooled to −20° C. in the refrigerator. The first crop of solid material was 77 g. The filter cake was rinsed again with THF (2×500 ml) and concentrated to an oil with solid. Addition of hexane (300 ml) gave another 54 g of product for a total of 131 g (79%). ¹HNMR (CDCl₃, 400 MHz): d (ppm) 5.54 (s, 1H), 5.45 (s, 1H), 4.65 (dd, 11.5, 4.0, 1H), 2.71 (d, 4.0, 1H), 2.48 (dd, 11.5, 17.0, 1H), 1.97 (t, 6.5, 2H), 1.81 (m, 2H), 1.79 (s, 3H), 1.76 (s, 3H) 1.55–1.63(m, 2H), 1.41–1.53 (m, 2H). 1.11 (s, 3H), 0.97 (S, 3H). IR (KBr, cm⁻¹): 3377, 2935, 2908, 1037. mp 147°–149° C.

(2Z,4E)-3-Methyl-5-(2,6,6-trimethylcyclohexen-1-yl)-2,4-pentadieneal (IV) where R¹ is methyl and R² is hydrogen): To 1 L of 1,2-dichlorethane was added lactol (119 grams) and 100 μL of concentrated HCl (38%) with constant stirring at room temperature. The reaction was heated to bring the solution to reflux and proceeds very quickly. The reaction is monitored by tlc (40% Dimethyl ether/Hexane). After 35 m the reaction was quenched with 400 mL of saturated NaHCO₃. After separation of layers the resulting red organic layer was dried over MgSO₄ and concentrated in vacuo to yield the desired aldehyde as a red oil. This oil was taken up in 500 ml of hexane and 120 g of silica gel (230–400 mesh) added. The solution was filtered, rinsed with another 500 ml of hexane, and concentrated to an orange oil (100.2 grams, 91%). An alternate procedure for production of the aldehyde is as follows: To a solution of 250 ml of 1,2-dichloroethane was added 30 g of the lactol and 125 ml of 1N HCl solution. The two phase solution was heated to 40° C. and monitored by TLC. The reaction was found to be complete after 12.5 hours. The reaction was quenched by the separation of layers and 500 ml of saturated Na₂CO₃ carefully added to the organic layer with stirring. The aqueous layer was washed with two 100 ml portions of dichloromethane and the collective organic layers washed once with brine. The organic solution was then dried over K₂CO₃ (anhydrous) and concentrated in vacuo to afford a red-orange oil. The crude product was diluted with hexanes (125 ml) and to this solution was added silica gel (30 g). The slurry was filtered and the silica rinsed until no more color came through the filter. The solution was concentrated in vacuo to afford 26 grams (94%) of clean product as a yellow-orange oil. ¹HNMR (CDCl₃, 400 MHz): d (ppm) 10.16 (d, 8.0, 1H), 7.08 (d, 16.0, 1H), 6.63 (d, 15.0, 1H), 5.86 (d, 8.0, 1H), 2.12 (s, 3H), 2.05 (t, 6.0, 2H), 1.75 (s, 3H), 1.57–1.75 (m, 2H), 1.40–1.53 (m, 2H), 1.05 (s, 6H). IR (film, cm⁻¹): 2930, 1667.

Ethyl 3,7-dimethyl-9-(2,6,6-trimethylcyclohexen-1-yl)-2-trans-4-trans-6-cis-8 -trans-nonatetraenoate (V, where R¹ and R³ are methyl and R² is hydrogen): A solution of 233 ml of tetrahydrofuran, 276 ml of 2,6-dimethylpiperidineurea and the phosphonate (109.4 grams) was cooled to –30° C. by use of a CO₂/acetone bath. Into this solution was added n-Buli (180 ml, 2.3M in hexane), dropwise. The reaction solution was cooled and allowed to stir at –78° C. for 0.25 hour before the aldehyde (75.4 g, 345 mmol) was added in 50 ml of tetrahydrofuran. The reaction was stirred at –78° C. for another 0.5 hours, then quenched by the addition of 200 ml of saturated ammonium chloride solution. The aqueous solution was extracted with diethylether (3×500 ml), and the combined organic extracts washed with brine and dried over magnesium sulfate. The crude reaction products (primarily 9-cis-13-trans retinoate and 9,13-di-cis-retinoate) were collected by concentration in vacuo to give a red-orange oil. The crude ester was taken up in 100 ml of 20% Et₂O/Hexane and filtered through 500 g of silica gel (230–400 mesh) which was rinsed with another 700 ml of eluent. The ester was concentrated to an orange oil (100.4 g, 93%) which looked very clean by NMR. The 13 E/Z ratio was >15:1. ¹HNMR (CDCl₃, 400 MHz); d (ppm) 7.08 (dd, 15, 11.3, 1H), 6.65 (d, 16, 1H), 6.29 (d, 15, 1H), 6.23 (d, 15, 1H), 6.06 (d, 11.3, 1H), 5.77 (s, 1H), 4.17 (q, 7, 2H), 2.34 (s, 3H), 2.05 (t, 7, 2H), 2.00 (m, 3H). 1.75 (s, 3H), 1.61–1.68 (m, 2H), 146–151 (m, 2H), 1.29 (t, 7, 3H), 104 (s, 6H). IR (film, cm⁻¹): 2928, 1709.

3,7-dimethyl-9-(2,6,6-trimethylcyclohexen-1-yl)-2-trans-4-trans-6-cis-8-trans-nonatetraenoic acid (VI, where R¹ and R³ are methyl and R² is hydrogen): The ester (100.4 grams) was slurred in 700 ml of ethanol. To this solution was added 700 ml of 14 wt. % NaOH/water (100 g NaOH) and the solution heated to 60° C. for 1 hour. Following the hydrolysis by TLC (25% ethyl acetate/hexane), one could see that the hydrolysis was incomplete. The solution was heated for another 2 hours and at this time appeared to be complete (TLC). The solution was allowed to cool, extracted with hexane (3×250 ml), and then cooled to 0° C., at which point it was acidified with 3N HCl to pH 2. The yellow-orange solid that precipitated from the aqueous solution was filtered, rinsed with water (2 liters), and then dissolved up in 1 liter THF/Et₂O (3:1). The organic solution was washed with brine and dried over magnesium sulfate. Concentration in vacuo gave 83.3 g of a light yellow solid (80.3% from aldehyde). ¹HNMR (CDCl₃, 400 MHz): d (ppm) 7.20 (dd, 11.0, 15.0, 1H), 6.65 (d, 16.0, 1H), 6.28 (d, 16.0, 1H), 6.25 (d, 15.0, 1H), 6.06 (d, 11.0, 1H), 5.80 (s, 1H), 2.35 (s, 3H), 2.05 (t, 6.6, 2H), 2.01 (s, 3H), 1.75 (s, 3H), 1.64 (m, 2H), 1.49 (m, 2H). 1.04 (s, 6H). IR (KBr, cm⁻¹): 2914, 1670, 1583. mp 188°–190° C. UV (MeOH): λ max=343 (37,800). Analysis Theoretical C:79.95, H: 9.39, O: 10.65 Found C:79.97, H:9.38, O:10.66.

While the preferred embodiments have been described and illustrated, various substitutions and modifications may be made thereto without departing from the scope of the invention. Accordingly, it is to be understood that the present invention has been described by way of illustration and not limitation.

We claim:

1. A method for producing a cis-olefin, comprising:
combining a lactol of the formula

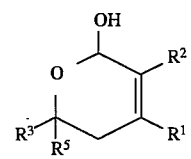

with acid and solvent reactants;
heating said reactants; and
quenching and separating the predominant resulting aldehyde product having the formula

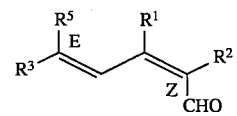

wherein R¹ represents a lower or branched alkyl having 1–12 carbons, or phenyl, and can be methyl only if R² is a hydrogen or a lower alkyl having 1–8 carbons, R² represents hydrogen, a lower alkyl having 1–8 carbons, or halogen, or R¹ and R² taken together form a phenyl, cyclohexyl, or cyclopentyl ring, R³ represents a lower alkyl having 1–8 carbons, polyene compounds of the formula R¹—CH=CH—

C($R^1$)=CH—(E or Z orientation), cycloalkyl, or aryl, and $R^5$ represents hydrogen, a lower alkyl having 1–8 carbons, or halogen.

2. The method of claim 1 wherein $R^1$ is methyl, $R^2$ is hydrogen, $R^3$ is 2,6,6-trimethylcyclohexen-1-yl, and $R^5$ is hydrogen.

3. The method of claim 1 wherein said acid is selected from the group consisting of para-toluene sulfonic acid, pyridinium hydrochloride trichloro- or trifluoro-acetic acid, acetic acid, sulfuric acid, nitric acid, tartaric acid, oxalyic acid, and hydrochloric acid.

4. The method of claim 1 wherein said solvent is selected from the group consisting of chlorinated solvents, apolar solvents, and coordinating solvents.

* * * * *

UNITED STATES PATENT AND TRADEMARK OFFICE
CERTIFICATE OF CORRECTION

PATENT NO. : 5,567,855
DATED : October 22, 1996
INVENTOR(S) : WHITE et al.

It is certified that error appears in the above-indentified patent and that said Letters Patent is hereby corrected as shown below:

On title page, item [63], under the Related U.S. Application Data section, change "Apr. 21, 1996" to --Apr. 21, 1993--.

Column 2, line 14, change "manufacuted" to --manufactured--.

Column 2, line 28, change "Generatin" to --Generation--.

Column 3, lines 50-55, change

Column 4, line 54, change "Not" to --not--.

Column 4, line 55, change "hydrofluoriic" to --hydrofluoric--.

UNITED STATES PATENT AND TRADEMARK OFFICE
CERTIFICATE OF CORRECTION

PATENT NO. : 5,567,855
DATED : October 22, 1996
INVENTOR(S) : WHITE et al.

It is certified that error appears in the above-identified patent and that said Letters Patent is hereby corrected as shown below:

Column 6, line 52, change "CH2Cl2" to --$CH_2Cl_2$--.

Signed and Sealed this

Twenty-first Day of April, 1998

Attest:

BRUCE LEHMAN

Attesting Officer

Commissioner of Patents and Trademarks